United States Patent
Bene

[19]
[11] Patent Number: 6,123,847
[45] Date of Patent: Sep. 26, 2000

[54] DEVICE AND PROCESS FOR REGULATING THE SODIUM CONCENTRATION IN A DIALYSIS LIQUID WITH A VIEW TO A PRESCRIPTION

[75] Inventor: Bernard Bene, Irigny, France

[73] Assignee: Hospal Industrie, Meyzieu, France

[21] Appl. No.: 09/137,120

[22] Filed: Aug. 20, 1998

[30] Foreign Application Priority Data

Aug. 21, 1997 [FR] France ................................. 97 10671

[51] Int. Cl.⁷ ........................... B01D 61/30; B01D 61/32
[52] U.S. Cl. ..................... 210/646; 210/96.2; 210/103; 210/321.71; 210/739; 604/4.1; 604/65; 604/66
[58] Field of Search ................. 210/85, 87, 96.1, 210/103, 137, 321.65, 321.71, 646, 647, 739, 929, 96.2; 604/4–6, 65–67, 4.01, 5.01, 6.09, 6.11

[56] References Cited

U.S. PATENT DOCUMENTS

| | | | |
|---|---|---|---|
| 4,923,613 | 5/1990 | Chevallet | 210/647 |
| 5,178,763 | 1/1993 | Delauney | 210/647 |
| 5,346,472 | 9/1994 | Keshaviah et al. | 604/65 |
| 5,366,630 | 11/1994 | Chevallet | 210/646 |
| 5,470,483 | 11/1995 | Bene et al. | 210/646 |
| 5,567,320 | 10/1996 | Goux et al. | 210/739 |
| 5,578,223 | 11/1996 | Bene et al. | 210/87 |
| 5,744,031 | 4/1998 | Bene | 210/646 |
| 5,938,938 | 8/1999 | Bosetto et al. | 210/646 |

FOREIGN PATENT DOCUMENTS

| | | |
|---|---|---|
| 516152 | 12/1992 | European Pat. Off. . |
| 0 532 433 | 3/1993 | European Pat. Off. . |
| 0 658 352 | 6/1995 | European Pat. Off. . |
| 2680975 | 12/1993 | France . |
| 2680976 | 12/1993 | France . |
| 41 14 908 | 11/1992 | Germany . |

*Primary Examiner*—Joseph W. Drodge
*Attorney, Agent, or Firm*—Finnegan, Henderson, Farabow, Garrett & Dunner, L.L.P.

[57] ABSTRACT

Dialysis apparatus including:

structure (14) for preparing a dialysis liquid containing sodium, comprising structure (18) for regulating the sodium concentration;

a dialysis liquid circuit comprising a feed line (12) and a discharge line (13), the feed line (12) having one end connected to the structure (14) for preparing dialysis liquid, and another end which can be connected to a dialyser (1), the discharge line (13) having an end which can be connected to the dialyser (1);

structure (9, 10, 12) for infusing a patient with an infusion solution containing sodium and a substance A at determined concentrations [Na⁺]sol and [A]sol;

structure (32) for determining the sodium concentration [Na⁺]dial of the dialysis liquid so that the patient's body tends towards a desired sodium concentration [Na⁺]des, as a function of the dialysance D of the dialyser (1) for sodium, of the desired sodium concentration [Na⁺]des inside the patient's body, of the infusion flow rate Qinf, and of the sodium concentration [Na⁺]sol of the infusion solution;

control structure (32) for driving the structure (18) for regulating the sodium concentration of the dialysis liquid such that this concentration is equal to the determined concentration [Na⁺]dial.

15 Claims, 1 Drawing Sheet

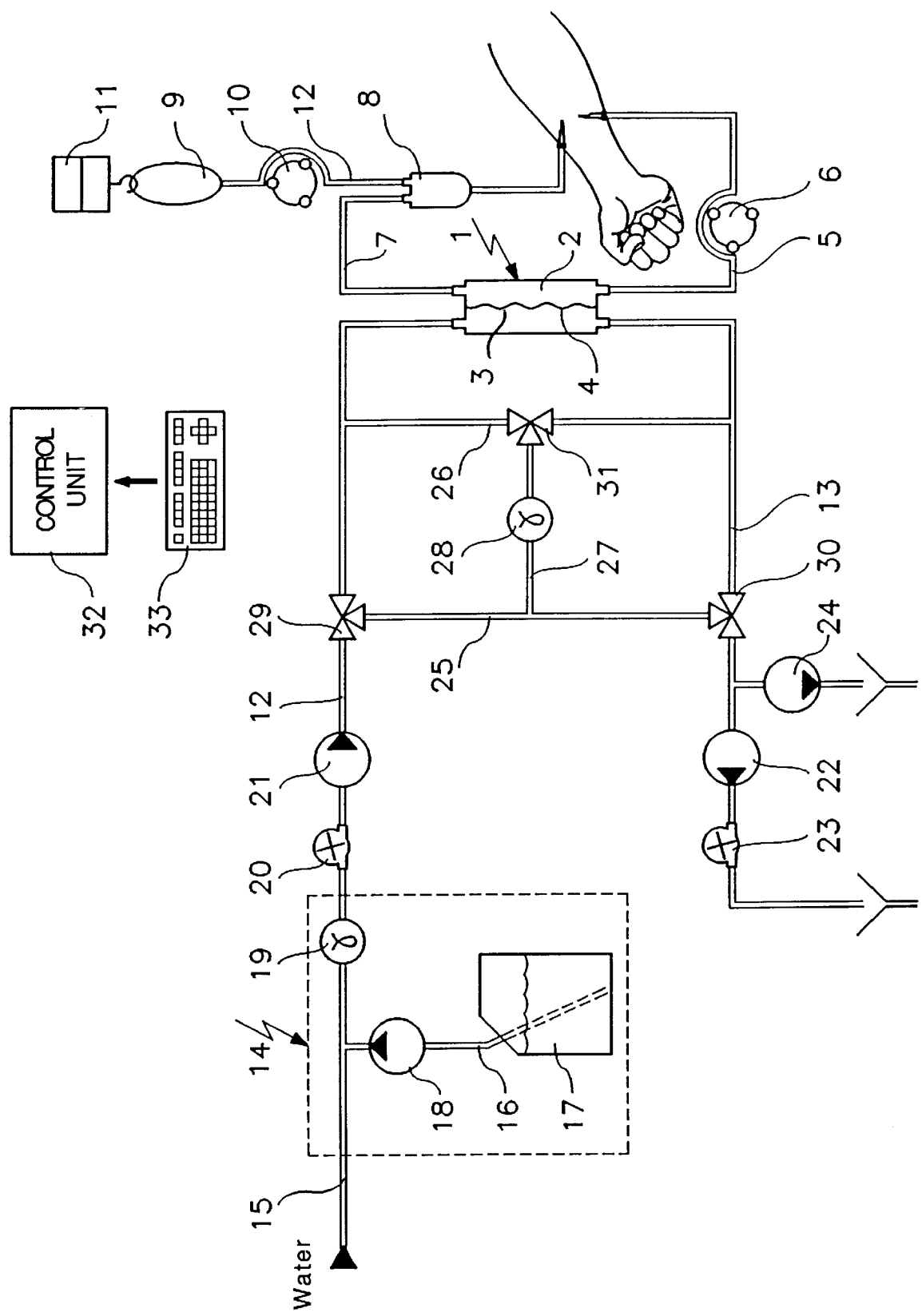

DEVICE AND PROCESS FOR REGULATING THE SODIUM CONCENTRATION IN A DIALYSIS LIQUID WITH A VIEW TO A PRESCRIPTION

BACKGROUND OF THE INVENTION

1. Field of the Invention

The present invention relates to dialysis apparatus and a process for regulating the concentration of sodium in a dialysis liquid with a view to a prescription.

2. Description of the Related Art

The kidneys fulfill many functions, including the removal of water, the excretion of catabolites (or waste from the metabolism, for example urea and creatinine), the regulation of the concentration of the electrolytes in the blood (sodium, potassium, magnesium, calcium, bicarbonates, phosphates, chlorides) and the regulation of the acid/base equilibrium within the body, which is obtained in particular by the removal of weak acids (phosphates, monosodium acids) and by the production of ammonium salts.

In individuals who have lost the use of their kidneys, since these excretion and regulation mechanisms no longer work, the body accumulates water and waste from the metabolism and exhibits an excess of electrolytes (in particular sodium), as well as, in general, acidosis, the pH of the blood plasma shifting towards 7 (the blood pH normally varies within narrow limits of between 7.35 and 7.45).

In order to overcome renal dysfunction, resort is conventionally made to a blood treatment involving extracorporeal circulation through an exchanger having a semipermeable membrane (haemodialyser) in which the patient's blood is circulated on one side of the membrane and a dialysis liquid, comprising the main electrolytes of the blood in concentrations close to those in the blood of a healthy subject, is circulated on the other side. Furthermore, a pressure difference is created between the two compartments of the haemodialyser which are delimited by the semipermeable membrane, so that a fraction of the plasma fluid passes by ultrafiltration through the membrane into the compartment for the dialysis liquid.

The blood treatment which takes place in a haemodialyser as regards waste from the metabolism and electrolytes results from two mechanisms of molecular transport through the membrane. On the one hand, the molecules migrate from the liquid where their concentration is higher to the liquid where their concentration is lower. This is diffusive transport or dialysis. On the other hand, certain catabolites and certain electrolytes are entrained by the plasma fluid which filters through the membrane under the effect of the pressure difference created between the two compartments of the exchanger. This is convective transport.

Three of the abovementioned functions of the kidney, namely the removal of water, the excretion of catabolites and the regulation of the electrolytic concentration of the blood, are therefore performed in a conventional blood treatment device by the combination of dialysis and blood filtration (this combination is referred to as haemodialysis).

As regards the regulation of the acid/base equilibrium inside the body, the approach adopted to overcome renal deficiency is to act on a mechanism by which the acid/base equilibrium inside the body is regulated, this mechanism consisting of the buffer systems of the blood, the main one of which comprises carbonic acid, as a weak acid, associated with its alkali salt, bicarbonate. This is why, in order to correct acidosis in a patient suffering from renal insufficiency, he is administered with bicarbonate via the vascular route, directly or indirectly, during a haemodialysis session.

The administration is indirect when the bicarbonate is involved in the composition of the dialysis liquid and passes into the blood by diffusion. One drawback of this method is connected with the fact that bicarbonate precipitates with calcium and magnesium, which belong to the conventional components of a dialysis liquid. In order to limit this reaction, an acid (acetic acid) is added to the dialysis liquid in order to lower its pH, which has the side effect of increasing the partial pressure of carbon dioxide in it, and has the undesirable consequence of inducing in the patient the discomfort resulting from the excess of this gas in his blood. Furthermore, in view of the maximum acceptable concentration of acid in the dialysis liquid, calcium deposits are produced in the circuits of the dialysis machine, and these need to be removed.

The administration of the bicarbonate is direct when the dialysis liquid is free of bicarbonate and the patient is infused with a sodium bicarbonate solution. This method has the benefit that it avoids having to combine, in the same treatment liquid, the substances which precipitate in the absence of acid. However, it poses the as yet unsolved problem of regulating the sodium concentration in the dialysis liquid so that the patient's body tends towards a determined sodium concentration. This is because, when the patient is infused with sodium bicarbonate with a view to reaching a determined bicarbonate concentration inside the patient's body, an amount of sodium is introduced therein which has not to date been taken into consideration, or has been taken into consideration only empirically, when the sodium concentration of the dialysis liquid is fixed. In other words, with the existing systems used for implementing the method which has just been described, no provision is made for regulating both the infusion flow rate of the sodium bicarbonate solution and the sodium concentration of the dialysis liquid such that the patient's body tends towards a precise predetermined concentration both of bicarbonate and of sodium.

SUMMARY OF THE INVENTION

The object of the invention is to provide a process for regulating the sodium concentration of a dialysis liquid, which allows the body of a patient receiving an infusion of a sodium salt solution to tend precisely towards a desired sodium concentration $[Na^+]des$.

To the this end, the invention provides a process for regulating the sodium concentration of a dialysis liquid to a determined value $[Na^+]dial$ so that the patient's body tends towards a desired sodium concentration $[Na^+]des$, the patient's blood and the dialysis liquid being circulated on either side of the semipermeable membrane of a dialyser, the patient furthermore receiving an infusion of a solution containing sodium and a substance A at determined concentrations $[Na^+]sol$ and $[A]sol$;

the process comprising the steps of:

- determining the sodium concentration $[Na^+]dial$ of the dialysis liquid as a function of the dialysance D of the dialyser for sodium, of the desired sodium concentration $[Na^+]des$ inside the patient's body, of the infusion flow rate $Qinf$, and of the sodium concentration $[Na^+]sol$ of the infusion solution; and
- adjusting the sodium concentration of the dialysis liquid to the determined concentration $[Na^+]dial$.

According to one characteristic of the invention, the step of determining the sodium concentration [Na$^+$]dial of the dialysis liquid consists in applying the formula:

$$[Na^+]\text{dial} = \frac{Qinf}{D}([Na+]des - [Na+]sol) + [Na+]des$$

According to another characteristic of the invention, the process furthermore includes the step of determining the dialysance D of the dialyser for sodium according to the steps of:

preparing and successively circulating through the dialyser at least two dialysis liquids having different conductivities;

taking at least two measurements of the conductivity of at least two dialysis liquids upstream and downstream of the dialyser;

calculating the dialysance D on the basis of the measured conductivity values (Cd1in, Cd1out, Cd2in, Cd2out) in at least two successively prepared dialysis liquids.

Preferably, the dialysance D of the dialyser for the sodium is calculated according to the following formula:

$$D = Qd \times \frac{(Cd1out - Cd1in) - (Cd2out - Cd2in)}{Cd2in - Cd1in}$$

where Qd is the flow rate of dialysis liquid.

According to yet another characteristic of the invention, the process furthermore comprises the steps of:

determining an infusion flow rate Qinf such that, at the end of the treatment session, the concentration of the substance A inside the patient's body tends towards a desired concentration [A]des;

adjusting the infusion flow rate to the determined flow rate Qinf.

Preferably, the infusion flow rate Qinf is calculated according to the following formula:

$$Qinf = Cl \times \frac{[A]des}{[A]sol - [A]des}$$

where Cl is the clearance of the dialyser for the substance A.

The invention also relates to a dialysis apparatus comprising:

means for preparing a dialysis liquid containing sodium, comprising means for regulating the sodium concentration;

a dialysis liquid circuit comprising a feed line and a discharge line, the feed line having one end connected to the means for preparing dialysis liquid, and another end which can be connected to a dialyser, the discharge line having an end which can be connected to the dialyser;

means for infusing a patient with an infusion solution containing sodium and a substance A at determined concentrations [Na$^+$]sol and [A]sol;

means for determining the sodium concentration [Na$^+$] dial of the dialysis liquid so that the patient's body tends towards a desired sodium concentration [Na$^+$] des, as a function of the dialysance D of the dialyser for sodium, of the desired sodium concentration [Na$^+$]des inside the patient's body, of the infusion flow rate Qinf, and of the sodium concentration [Na$^+$]sol of the infusion solution;

control means for driving the means for regulating the sodium concentration of the dialysis liquid such that this concentration is equal to the determined concentration [Na$^+$]dial.

BRIEF DESCRIPTION OF THE DRAWING

Other characteristics and advantages of the invention will become more clearly apparent on reading the following description. Reference will be made to the single appended figure, which schematically represents a haemodialysis system according to the invention.

DESCRIPTION OF THE PREFERRED EMBODIMENT

The haemodialysis system represented in the figure comprises a haemodialyser 1 having two compartments 2, 3 separated by a semipermeable membrane 4. A first compartment 2 has an inlet connected to a blood withdrawal line 5, in which a circulation pump 6 is arranged, and an outlet connected to a blood return line 7 in which a bubble trap 8 is inserted.

An infusion device, comprising a pump 10 and a balance 11, is provided for injecting the contents of an infusion liquid bag 9 into the bubble trap 8. The infusion liquid is a sterile solution of sodium bicarbonate in which the bicarbonate concentration [HCO3-]sol (that is to say also the sodium concentration [Na$^+$]sol) is known. The bag 9 is suspended from the balance 11 and is connected to the bubble trap 8 by a line 12 in which the infusion pump 10 is arranged. The balance 11 is used to drive the pump 10 such that the flow rate of the infusion liquid is equal to a target flow rate.

The second compartment 3 of the haemodialyser 1 has an inlet connected to a feed line 12 for fresh dialysis liquid, and an outlet connected to a discharge line 13 for spent liquid (dialysis liquid and ultrafiltrate).

The feed line 12 connects the haemodialyser 1 to a device 14 for preparing dialysis liquid, comprising a main line 15 whose upstream end is intended to be connected to a source of running water. A secondary line 16 is connected to this main line, the free end of which secondary line is intended to be immersed in a container 17 for a concentrated saline solution containing sodium chloride, calcium chloride, magnesium chloride and potassium chloride. A pump 18 is arranged in the secondary line 16 in order to allow the metered mixing of water and concentrated solution in the main line 15. The pump 18 is driven on the basis of the comparison between 1) a target conductivity value for the mixture of liquids formed where the main line 15 joins the secondary line 16, and 2) the value of the conductivity of this mixture measured by means of a conductivity probe 19 arranged in the main line 15 immediately downstream of the junction between the main line 15 and the secondary line 16.

The feed line 12 forms an extension of the main line 15 of the device 14 for preparing dialysis liquid. Arranged in this feed line, in the direction in which the liquid circulates, there are a first flow meter 20 and a first circulation pump 21.

The downstream end of the discharge line 13 for spent liquid is intended to be connected to the drain. Arranged in this line, in the direction in which the liquid circulates, there are a second circulation pump 22 and a second flow meter 23. An extraction pump 24 is connected to the discharge line 13, upstream of the second circulation pump 22. The extraction pump 24 is driven in such a way 30 that its delivery rate is equal to a target value for the ultrafiltration rate in the haemodialyser 1.

The feed line 12 and the discharge line 13 are connected by first and second branch lines 25, 26, which are connected together by a junction line 27 in which a conductivity probe 28 is arranged. The first branch line 25 is connected to the feed line 12, downstream of the first circulation pump 21, via a first three-way valve 29, and it is connected to the discharge line 13, upstream of the second circulation pump 22, via a second three-way valve 30. The second branch line 26 and the junction line 27 are connected via a third three-way valve 31.

The haemodialysis system represented in FIG. 1 also comprises a calculation and control unit 32. This unit is connected to a user interface (alphanumeric keyboard) 33 through which it receives instructions, such as various target flow rate values (blood flow rate Qb, dialysis liquid flow rate Qd and, where appropriate, infusion liquid flow rate Qinf), dialysis liquid conductivity values Cd1 in, Cd2 in, treatment duration value T, and weight loss value WL. The calculation and control unit 32 furthermore receives information output by the measuring instruments of the system, for example the flow meters 20, 23, the conductivity probes 19, 28 and the balance 11. On the basis of the instructions received and the operating modes and algorithms which have been programmed, it drives the active components of the system, such as the pumps 6, 10, 18, 21, 22, 24 and the valves 29, 30, 31.

The haemodialysis system which has just been described operates as follows.

After the extracorporeal blood circuit has been rinsed and filled with sterile saline solution, it is connected to the patient and the blood pump 6 is turned on at a predetermined delivery rate Qb, for example 200 ml/min.

At the same time, the pump 18 for metering concentrated solution, the pumps 21, 22 for circulating dialysis liquid and the extraction pump 24 are turned on. The delivery rate of the metering pump 18 is initially regulated so that the dialysis liquid has a sodium concentration (that is to say also a conductivity) such that the sodium concentration inside the patient's body evolves approximately towards a desired concentration. The delivery rate Qd of the circulation pump 21 arranged in the feed line 12 is regulated to a fixed value (for example 500 ml/min), while the delivery rate of the circulation pump 22 arranged in the discharge line 13 is continuously adjusted so that the flow rate measured by the second flow meter 23 is equal to the flow rate measured by the first flow meter 20. The delivery rate of the extraction pump 24, which causes the ultrafiltration of the plasma fluid, is equal to the delivery rate Qinf of the infusion pump 10 plus the weight loss flow rate (calculated on the basis of the weight WL which the patient is prescribed to lose and the duration T of the treatment session).

The valves 29, 30, 31 are arranged in such a way that the fresh dialysis liquid circulates in the junction line 27 and irrigates the conductivity probe 28.

The infusion pump 10 is initially turned on at a delivery rate Qinf, chosen empirically so that the bicarbonate concentration inside the patient's body evolves approximately towards a desired concentration [HCO3-]des. The delivery rate of the pump 10 is regulated precisely by means of the balance 11.

According to the invention, the delivery rate of the pump for concentrated solution 18 is adjusted continuously so that the sodium concentration [Na$^+$]dial of the dialysis liquid as measured by means of the conductivity probe 19, can make the sodium concentration inside the patient's body evolve precisely towards a desired value [Na$^+$]des. The sodium concentration [Na$^+$]dial of the dialysis liquid is calculated by the calculation unit 32 as a function of the dialysance D of the dialyser 1 for sodium, of the desired sodium concentration [Na$^+$]des inside the patient's body, of the infusion flow rate Qinf, and of the sodium concentration [Na$^+$]sol of the infusion solution. It can be calculated by applying the following formula:

$$[Na^+]dial = \frac{Qinf}{D}([Na+]des - [Na+]sol) + [Na+]des \quad (1)$$

The value of the dialysance D used in formula (1) may be a fixed value estimated empirically by the user of the dialysis system on the basis of the theoretical performance of the dialyser which is used, of the blood flow rate Qb and of the dialysis liquid flow rate Qd. In this case, the user supplies this value of the dialysance D to the calculation and control unit 32 before the treatment session.

Preferably, the value of the dialysance D used in formula (1) is an actual value determined by calculation, for example by implementing the following process, in which the successive steps are controlled by the control unit 32. With the three-way valves 29, 30, 31 being arranged in such a way that the fresh dialysis liquid irrigates the conductivity probe 28, the conductivity Cd1in of the fresh dialysis liquid corresponding to the prescription is measured and stored. The three valves 29, 30, 31 are then turned so that the conductivity probe 28 is irrigated by the spent liquid, and the conductivity Cd1out of this liquid is measured and stored. The delivery rate of the pump 18 for concentrate is then modified (increased or decreased) so that the conductivity of the dialysis liquid circulated is slightly different from the conductivity of the dialysis liquid of the prescription. For example, the conductivity of the second dialysis liquid is regulated so as to be 1 mS/cm greater or less than the conductivity of the first dialysis liquid (which is generally of the order of 14 mS/cm). As before, the conductivity Cd2in of the second dialysis liquid upstream of the dialyser 1 is measured and stored, after which the three-way valves 29, 30, 31 are again turned so that the conductivity probe 28 is irrigated by the spent liquid, and the conductivity Cd2out of the spent liquid is measured and stored. The actual dialysance D of the dialyser 1 can then be calculated by applying the following formula:

$$D = Qd \times \frac{(Cd1out - Cd1in) - (Cd2out - Cd2in)}{Cd2in - Cd1in} \quad (2)$$

Another process for calculating the actual dialysance D on the basis of measurements taken with two dialysis liquids having different conductivities is described in Patent Application EP 0 658 352.

The infusion flow rate Qinf involved in the calculation of the sodium concentration [Na+]dial of the dialysis liquid can be evaluated empirically by the user of the dialysis system so that the bicarbonate concentration inside the patient's body evolves approximately towards a desired concentration. In this case, the user supplies this fixed value of infusion flow rate to the calculation and control unit 32 before the treatment session.

Preferably, the infusion flow rate Qinf is calculated and is adjusted regularly so that the bicarbonate concentration in the blood tends precisely towards a desired value [HCO3-]des. As a general rule, the flow rate Qinf of the infusion solution can be calculated at any instant by applying the formula:

$$Qinf = Cl \times \frac{[HCO3^-]des}{[HCO3^-]sol - [HCO3^-]des} \quad (3)$$

where Cl is the clearance of the dialyser 1 for bicarbonate, which can be readily extrapolated from the dialysance D for sodium, irrespective of the way in which it is determined.

The invention does not apply only to the dialysis method which has just been described, in which the infusion solution comprises sodium bicarbonate and in which the dialysis liquid is free thereof. It applies in general to any dialysis method in which the dialysis liquid which is used contains sodium and in which the patient who is dialysed receives an infusion of a solution containing a sodium salt.

By way of example, in order to avoid the drawbacks of conventional dialysis with bicarbonate which were mentioned above, in which the dialysis liquid contains all the blood electrolytes and acetic acid, it is possible to employ the following treatment: the dialysis liquid is prepared from a concentrated solution of sodium chloride and sodium bicarbonate, and optionally potassium chloride (mixture of water and the concentrated solution by means of the variable-rate pump 18 of the device represented in the figure). Furthermore, the patient who is dialysed receives an infusion of a solution of sodium, magnesium, calcium and optionally potassium chloride. The potassium is involved either in the composition of the dialysis liquid or in the composition of the infusion solution. The composition of these liquids is particularly suited to treatment by haemodiafiltration in which the infusion flow rate is greater than 1 liter per hour.

Variants may be made to the invention which has just been described. Instead of a single conductivity probe, to which the fresh dialysis liquid and the spent liquid are successively applied, the dialysis liquid circuit may be equipped with two conductivity probes which are arranged in the dialysis liquid circuit, respectively upstream and downstream of the dialyser. The dialysis liquid circuit may also include only one conductivity probe, arranged downstream of the dialyser, in which case the two target conductivity values used for driving the concentrate pump 18 in order to prepare the first and second dialysis liquids are substituted in the formula indicated above for the conductivity values measured upstream of the dialyser.

What is claimed is:

1. Dialysis apparatus comprising:
    means for preparing a dialysis liquid containing sodium, comprising means for regulating the sodium concentration of the liquid;
    a dialysis liquid circuit comprising a feed line and a discharge line, the feed line having one end connected to the means for preparing dialysis liquid, and another end which can be connected to a dialyser, the discharge line having an end which can be connected to the dialyser;
    means for infusing a patient with an infusion solution containing sodium and a substance A at determined concentrations $(Na^+)sol$ and $(A)sol$;
    means for determining the sodium concentration $(Na^+)$ dial of the dialysis liquid so that the patient's body tends towards a desired sodium concentration $(Na^+)$ des, as a function of the dialysance D of the dialyser for sodium, of the desired sodium concentration $(Na^+)des$ inside the patient's body, of the infusion flow rate Qinf, and of the sodium concentration $(Na^+)sol$ of the infusion solution;
    control means for driving the means for regulating the sodium concentration of the dialysis liquid such that the concentration is equal to the determined concentration $(Na^+)dial$.

2. Apparatus according to claim 1, wherein the means for determining the sodium concentration $(Na^+)dial$ of the dialysis liquid comprises calculation means for calculating the concentration according to the formula:

$$(Na^+)dial = \frac{Qinf}{D}((Na^+)des - (Na^+)sol) + (Na^+)des.$$

3. Apparatus according to claim 1, further including means for determining the dialysance D of the dialyser for sodium.

4. Apparatus according to claim 3, wherein the means for determining the dialysance D of the dialyser for sodium compromises:
    means for measuring the conductivity of the dialysis liquid upstream and downstream of the dialyser; and
    means for calculating the dialysance D on the basis of at least two conductivity values measured respectively upstream and downstream of the dialyser in at least two successively prepared dialysis liquids.

5. Apparatus according to claim 4, wherein the means for calculating is configured to calculate the dialysance D of the dialyser for sodium according to the following formula:

$$D = Qd \times \frac{(Cd1out - Cd1in) - (Cd2out - Cd2in)}{Cd2in - Cd1in}$$

where Qd is the flow rate of dialysis liquid.

6. Apparatus according to claim 5, wherein the means for determining the infusion flow rate Qinf comprises calculation means for calculating the infusion flow rate Qinf according to the formula:

$$Qinf = Cl \times \frac{[A]des}{[A]sol - [A]des}$$

where Cl is the clearance of the dialyser for the substance A.

7. Apparatus according to claim 1 comprising:
    means for determining an infusion flow rate Qinf such that the concentration of the substance A inside the patient's body tends towards a desired concentration $(A)des$;
    means for regulating the infusion flow rate Qinf; and
    control means for driving the means for regulating the infusion flow rate such that the flow rate is equal to the flow rate Qinf.

8. Process for regulating the sodium concentration of a dialysis liquid to a determined value $(Na^+)dial$ so that a patient's body tends towards a desired sodium concentration $(Na^+)des$, the patient's blood and the dialysis liquid being circulated on either side of a semipermeable membrane of a dialyser, the patient furthermore receiving an infusion of a solution containing sodium and a substance A at determined concentrations $(Na^+)sol$ and $(A)sol$;
the process comprising the steps of:
    determining the sodium concentration $(Na^+)dial$ of the dialysis liquid as a function of the dialysance D of the dialyser for sodium, of the desired sodium concentration $(Na^+)des$ inside the patient's body, of the infusion flow rate Qinf, and of the sodium concentration (Na⁺) sol of the infusion solution; and adjusting the sodium concentration of the dialysis liquid to the determined concentration (Na⁺)dial.

9. Process according to claim 8, wherein the step of determining the sodium concentration (Na⁺)dial of the dialysis liquid includes applying the formula:

$$(Na^+)dial = \frac{Qinf}{D}(Na+)des - (Na+)sol) + (Na+)des.$$

10. Process according to claim 8, further including the step of determining the dialysance D of the dialyser for sodium according to the steps of:

preparing and successively circulating through the dialyser at least two dialysis liquids having different conductivities;

taking at least two measurements of the conductivity of the at least two dialysis liquids upstream and downstream of the dialyser; and calculating the dialysance D on the basis of the measured conductivity values (Cd1in, Cd1out, Cd2in, Cd2out) of the at least two dialysis liquids.

11. Process according to claim 10, wherein the step of calculating the dialysance D of the dialyser for sodium includes applying the following formula:

$$D = Qd \times \frac{(Cd1out - Cd1in) - (Cd2out - Cd2in)}{Cd2in - Cd1in}$$

where Qd is the flow rate of dialysis liquid.

12. Process according to claim 8, further comprising the steps of:

determining an infusion flow rate Qinf such that, at an end of a treatment session, the concentration of the substance A inside the patient's body tends towards a desired concentration (A)des; and adjusting the infusion flow rate to the determined flow rate Qinf.

13. Process according to claim 12, wherein the step of determining the infusion flow rate Qinf includes calculating the infusion flow rate Qinf according to the formula:

$$Qinf = Cl \times \frac{(A)des}{(A)sol - (A)des}$$

where Cl is the clearance of the dialyser for the substance A.

14. Process according to claim 13 wherein the clearance of the dialyser for the substance A is extrapolated from the dialysance D of the dialyser for sodium.

15. Process according to claim 8, wherein the substance A is bicarbonate.

* * * * *